United States Patent [19]

Lodder

[11] Patent Number: 4,893,253
[45] Date of Patent: Jan. 9, 1990

[54] METHOD FOR ANALYZING INTACT CAPSULES AND TABLETS BY NEAR-INFRARED REFLECTANCE SPECTROMETRY

[75] Inventor: Robert A. Lodder, Bloomington, Ind.
[73] Assignee: Indiana University Foundation, Bloomington, Ind.
[21] Appl. No.: 166,233
[22] Filed: Mar. 10, 1988
[51] Int. Cl.⁴ .................. G06F 15/20; G06F 15/42
[52] U.S. Cl. .................................. 364/497; 364/498
[58] Field of Search ............................ 364/496–499, 364/413.01, 413.02, 525; 250/338.1, 338.5, 339–343; 356/36, 51, 30, 319, 328, 334

[56] References Cited

U.S. PATENT DOCUMENTS

| | | | |
|---|---|---|---|
| 4,286,327 | 8/1981 | Rosenthal et al. | 364/498 |
| 4,399,361 | 8/1983 | Zanzucchi et al. | 250/341 |
| 4,466,076 | 8/1984 | Rosenthal | 364/498 |
| 4,496,839 | 1/1985 | Bernstein et al. | 250/341 |
| 4,540,282 | 9/1985 | Landa et al. | 356/328 |
| 4,633,087 | 12/1986 | Rosenthal et al. | 250/339 |
| 4,640,614 | 2/1987 | Roberts et al. | 250/341 |
| 4,652,756 | 3/1987 | Ryan et al. | 250/338.5 |
| 4,692,620 | 9/1987 | Rosenthal | 250/339 |
| 4,742,228 | 5/1988 | Bischoff | 356/36 |
| 4,785,184 | 11/1988 | Bien et al. | 250/339 |

OTHER PUBLICATIONS

Wetzel, D. L., "Near-Infrared Reflectance Analysis, Sleeper Among Spectroscopic Techniques", Anal. Chem., 55(12): 1165–1172 (1983).
Hadzija, B. W., et al., "Simple Techniques to Detect and Identify Phentermine Adulteration," Forensic Sci. Int'l., 23:143–147 (1983).
Efron, B., "Nonparametric estimates of standard error: The jackknife, the bootstrap . . .", Biometrika, 68(3)589–599 (1981).
Mark, H. L., et al., "Qualitative Near-Infrared Reflectance Analysis Using Mahalanobis Distances,"Anal. Chem., 57:1449–1456 (1985).
Mark, H., "Normalized Distances for Qualitative Near-Infrared Reflectance Analysis," Anal. Chem., 58:379–384 (1986).
Honigs, D. E., et al., "Number of Samples and Wavelengths Required for the Training Set . . .", Appl. Spectr. 38(6):844–847 (1984).
Honigs, D. E., et al., "Near-Infrared Spectrophotometric Methods Development with a Limited Number of Samples . . .", Appl. Spectr. 39(6): 1062–1065 (1985).
Lodder, R. A., "Quantile BEAST Attacks the False-Sample Problem in Near-Infrared Reflectance Analysis" Unpublished Manuscript 1987.

Primary Examiner—Parshotam S. Lall
Assistant Examiner—Kevin J. Teska
Attorney, Agent, or Firm—Kirkland & Ellis

[57] ABSTRACT

The BEAST method, when used in conjunction with NIRS data at as few as one or two wavelengths, is able to quickly detect a wide variety of adulterants in capsules, obviating the need to open them for analysis. The ability of this technique to detect the absence of components that should be present as well as the presence of components that should be absent enables it even to signal the presence of adulterants that have no near-infrared absorption. The technique generally comprises the steps of obtaining spectra for a training set of unadulterated samples, representing each specturm as a point in a hyperspace, creating a number of training set replicates and a bootstrap replicate distribution, calculating the center of the bootstrap replicate distribution, obtaining a spectrum for an adulterated sample, transforming this spectrum into a point in hyperspace, and identifying the adulterated sample as abnormal based on a relationship between the adulterated sample's hyperspatial point and the bootstrap replicate distribution.

3 Claims, 15 Drawing Sheets

THE TRAINING PROCESS

Distances of Spectra of Sodium Cyanide-containing Capsules from the Training-Set Spectral Cluster (in standard deviations)

4 wavelengths, 4-D space

Datril[b]

| NaCN(mg) | Green End[a] | White End[a] | Mixed In |
|---|---|---|---|
| 100 | 26.89 | 3.69 | 6.76 |
| 200 | 29.37 | 9.18 | 3.95 |
| 300 | 32.17 | 18.16 | 7.18 |
| 400 | 34.82 | 26.02 | 16.23 |

Anacin-3[c]

| NaCN(mg) | Blue End[a] | White End[a] | Mixed In |
|---|---|---|---|
| 100 | 11.57 | 2.30 | 1.52 |
| 200 | 7.51 | 8.15 | 3.27 |
| 300 | 9.86 | 15.50 | 5.09 |
| 400 | 16.99 | 18.03 | 11.26 |

Pure NaCN 30.91
32.70

4 wavelengths + weights, 5-D space

Anacin-3

| NaCN(mg) | Blue End[a] | White End[a] | Mixed In |
|---|---|---|---|
| 100 | 7.49 | 3.77 | 4.62 |
| 200 | 5.64 | 5.61 | 4.45 |
| 300 | 7.40 | 10.70 | 3.75 |
| 400 | 14.27 | 11.99 | 7.33 |

Pure NaCN 25.92
31.61 a. End of capsule into which adulterant was added
b. Mean total mass of capsule = 694 mg.
c. Mean total mass of capsule = 670 mg.

Fig. 15

False-Sample Sets for Hook's Cold Cap Capsules
Adulterated with Various Substances Distances from Unadulterated Capsule Training-Set Cluster for
Test Capsules (in standard deviations)

| Adulterant | Capsule 1 | Capsule 2 | Capsule 3 | Capsule 4 | Capsule 5 |
|---|---|---|---|---|---|
| NaF (100%): | 10.26 | 10.07 | 10.23 | 10.22 | 9.63 |
| $As_2O_3$ (100%): | 10.16 | 10.26 | 10.33 | 10.24 | 10.22 |
| Al (100%): | 6.96 | 7.24 | | | |
| Al (20%)[a]: | 3.58 | 4.90 | | | |
| $Fe_2O_3$ (100%): | 8.47 | 8.56 | | | |
| $Fe_2O_3$ (30%)[a]: | 6.65 | 7.47 | 7.12 | | |
| NaCN (100%): | 10.57 | | | | |
| Empty capsule: | 11.09 | | | | | a. The remainder of the capsule was filled with the ordinary capsule contents, i.e., cold remedy.

Fig. 4

Distances of Anacin-3 Validation Samples from the Training-Set Cluster (distances in SDs for each capsule)

4 wavelengths, 4-D space

| | | |
|---|---|---|
| 1.82 | 2.38 | 1.32 |
| 1.38 | .68 | 1.10 |
| 2.14 | 1.17 | .87 |
| 1.66 | 1.84 | 1.12 |
| 1.46 | | |

4 wavelengths + weights, 5-D space

| | | |
|---|---|---|
| 2.23 | 1.02 | 1.84 |
| 2.33 | 1.11 | 1.40 |
| 2.44 | 1.74 | .77 |
| 2.74 | 2.04 | 1.97 |
| 1.76 | | |

Fig. 14

METHOD FOR ANALYZING INTACT CAPSULES AND TABLETS BY NEAR-INFRARED REFLECTANCE SPECTROMETRY

BACKGROUND OF THE INVENTION

Co-pending application Ser. No. 07/165,751 filed on March 9, 1988 is incorporated herein by reference.

A. FIELD OF THE INVENTION

This invention relates to a noninvasive and nondestructive method for screening irregular or inhomogeneous samples and, in particular, for screening encapsulated drugs and tablets for contaminants and imperfections using near-infrared reflectance analysis and a nonparametric clustering algorithm. This method permits a rapid noninvasive detection of a variety of contaminants placed in samples, including sodium cyanide and potassium cyanide.

B. PRIOR ART

The well-publicized adulteration of nonprescription capsules with poisons has emphasized to the need for rapid, noninvasive and nondestructive methods of screening over-the-counter drugs. In 1982, for example, potassium cyanide appeared in capsules of the product acetaminophen sold under the trademark EXTRA STRENGTH TYLENOL ® in the Chicago area, and resulted in seven deaths. Subsequently, a number of "copycat" incidents occurred, involving strychnine, mercuric chloride and sodium hydroxide in capsules, hydrochloric acid in eyedrops and sodium fluoride in an artificial sweetener.

The number of cases of product tampering appears to be increasing. The cost of recalls is astronomical. For example, the cost to Johnson and Johnson, the maker of TYLENOL, acetaminophen is estimated to be $150 million for its most recent recall.

Following the 1982 TYLENOL incident, the Food and Drug Administration (FDA) collected and tested two million capsules of TYLENOL in a search for adulterated bottles of the drug. While the FDA did not publicize all of its methods, several techniques have been reported for various capsule analyses. The first of these analyses included such simple methods as inspection by visual appearance and odor. For example, in the TYLENOL case, the capsules had been grossly adulterated with 500 to 800 milligrams of potassium cyanide. Because adulterants like cyanides frequently have crystal sizes and shapes different from those of drugs like acetaminophen, the adulteration could be visually observed. In addition, potassium cyanide is deliquescent; therefore, a readily identifiable distortion and discoloration of some of the adulterated capsules could be seen. Potassium cyanide also can be detected by odor because it emits a smell of bitter almonds. This physical method, of course, is subject to human error which may result in tainted capsules not being detected. Further, this procedure is clearly unsuitable for detecting lower-level contamination.

Ultra Violet ("UV") spectrometry of capsules also has been utilized to identify substitution of phentermine, phenylpropanolamine and caffeine in drugs. In addition, thin-layer chromatography and microcrystal tests have been used to detect counterfeit IONAMIN phentermine capsules.

Moreover, X-ray spectrometry, using grain inspection or clinical mammographic instrumentation, has been employed to detect cyanide in TYLENOL acetaminophen capsules. Analysis of capsules for cyanide also has been performed using differential pulse polarography of cyanide reduction (at about −0.3 V vs. SCE).

Finally, inductively-coupled plasma atomic emission spectrometry has been used to obtain an elemental "fingerprint" of tainted capsules in an effort to trace the source of the adulterant.

With the possible exception of X-ray methods, which are often expensive to implement, all of the above techniques require sample capsules to be opened and their contents emptied for analysis or tablets to be ground for analysis. Clearly, a noninvasive, nondestructive, more economical method of analyzing the contents of suspect capsules or similar products directly through the walls of the container or of analyzing an intact tablet would be desirable for rapid screening in large numbers.

Therefore, it is an object of the present invention to provide a rapid, noninvasive, nondestructive method for detecting adulterants and imperfections in encapsulated drugs and tablets.

It is another object of the present invention to provide a method, utilizing near-infrared reflectance spectroscopy and a nonparametric clustering algorithm, for detecting adulterants in encapsulated drugs or tablets.

It is a further object of the present invention to provide a quality control method for detecting inhomogeneity and imperfections in samples using near-infrared reflectance analysis and a nonparametric algorithm.

C. BRIEF DESCRIPTION OF THE FIGURES

FIG. 1 shows two compounds, A and B, the spectra of which are measured at two discrete wavelengths. Uncertainty in the measurements at each wavelength is represented by taking 1000 replicate spectra of both A and B, resulting in clusters of points varying about A and B. The centers of the clusters represent the best point estimate of the spectra of A and B. A line is defined by the centers of the two clusters, and the locus of all points within a user-specified distance of this line forms a cylinder in the space of three or more dimensions.

FIG. 4 is a summary of data collected for adulterated HOOK'S COLD CAPS phenylpropanolamine hydrochloride and chlorpheniramine maleate Capsules.

Figure 5:
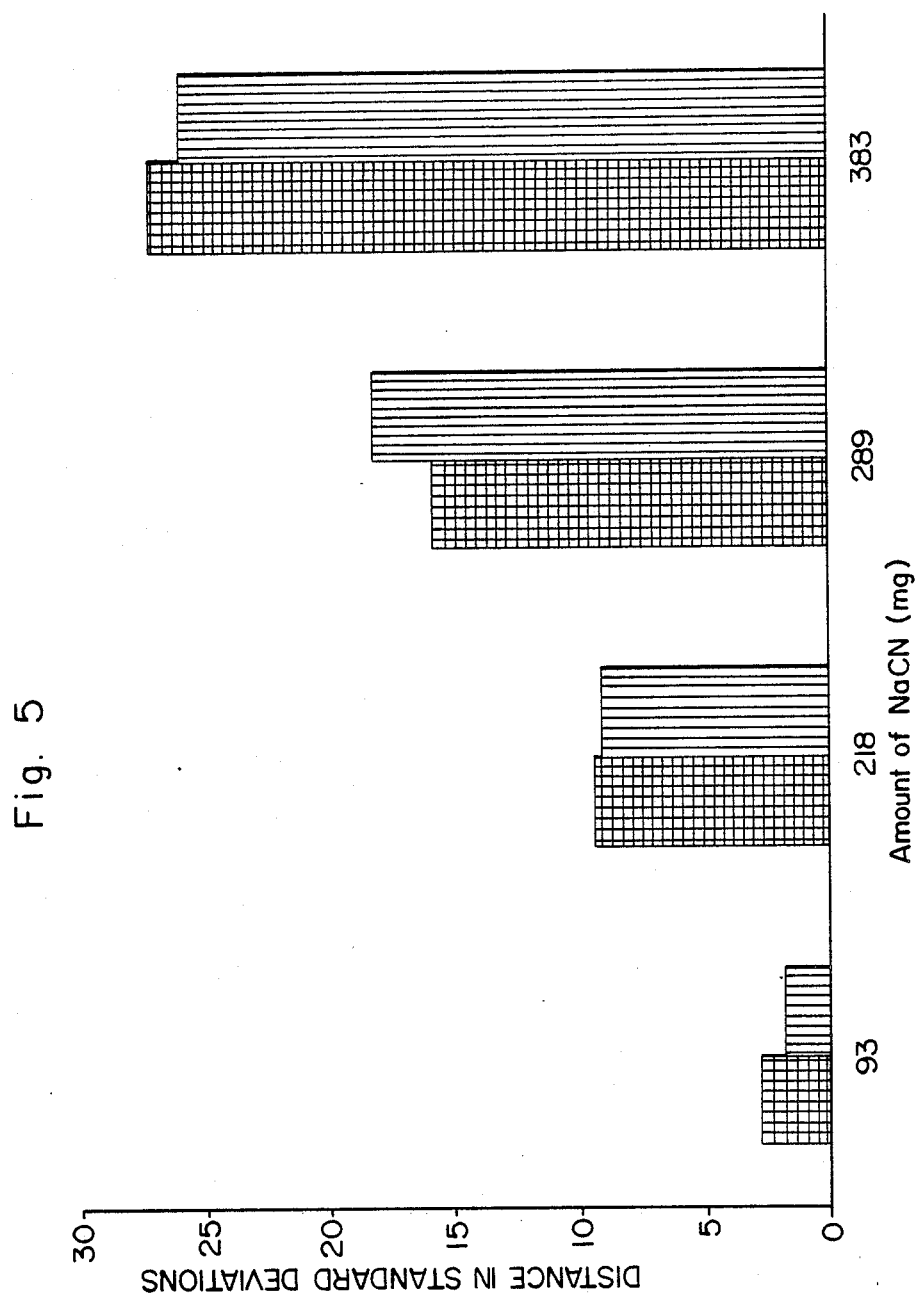

FIG. 5 shows the theoretical and actual response for an adulterant packed in the lower end of a DATRIL acetaminophen capsule in the conical reflector. The first bar (#) represents the scaled sodium cyanide theoretical distance response of the Bootstrap Error Adjusted Single Sample Technique (the "BEAST") for an adulterated capsule filled from the bottom to the top in 100 milligram steps. The second bar (| | |) represents the actual response of the BEAST for sodium cyanide packed into the white (bottom) end of a DATRIL acetaminophen capsule.

Figure 6:
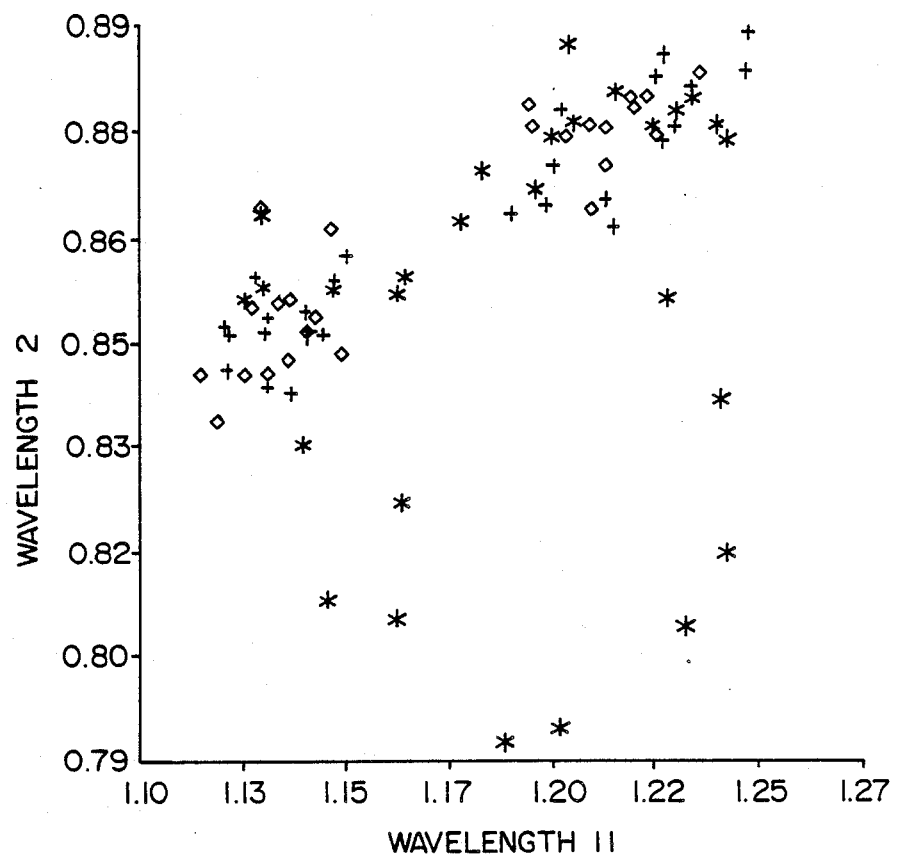

FIG. 6 shows spectral clusters of ANACIN-3 acetaminophen capsules obtained at two discrete wavelengths with the conical reflector, and with both orientations (colored end up and colored end down). The cluster on the left is formed by readings taken with the colored end up in the cone, while the cluster on the right is formed from the same capsules, read with the colored end down in the reflector. Training-set capsule (○); validation-set capsule (+) and cyanide-containing capsule (*).

Figure 7:
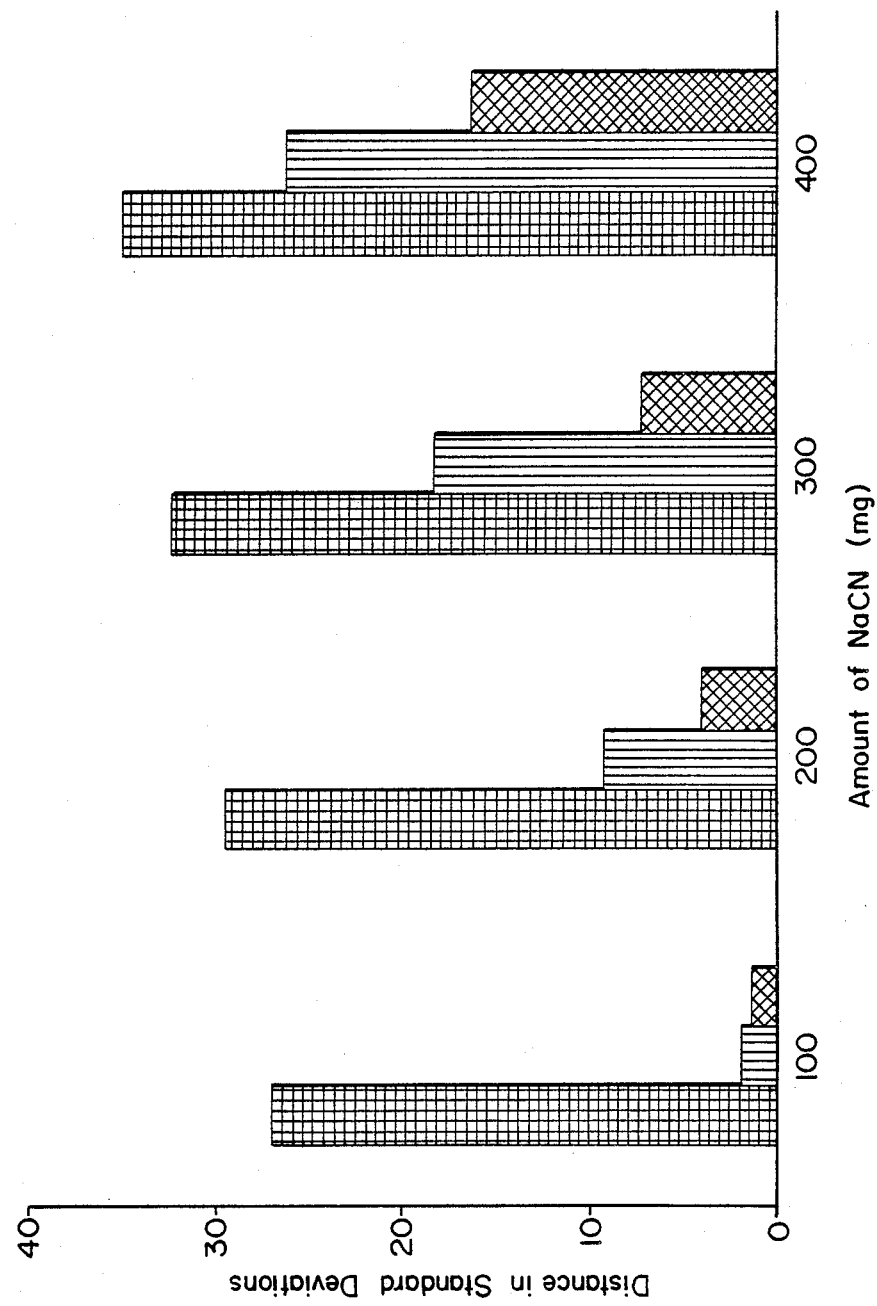

FIG. 7 shows DATRIL acetaminophen capsules analyzed with the colored end up in the reflector cone, containing approximately 100, 200, 300, and 400 milligrams sodium cyanide packed in three configurations: in the colored end (#), in the white end (|||) and mixed throughout the capsule (XXX). The distance in standard deviations is given in terms of the training set of unadulterated Datril capsules in the direction of the sodium cyanide-containing capsule.

Figure 8:
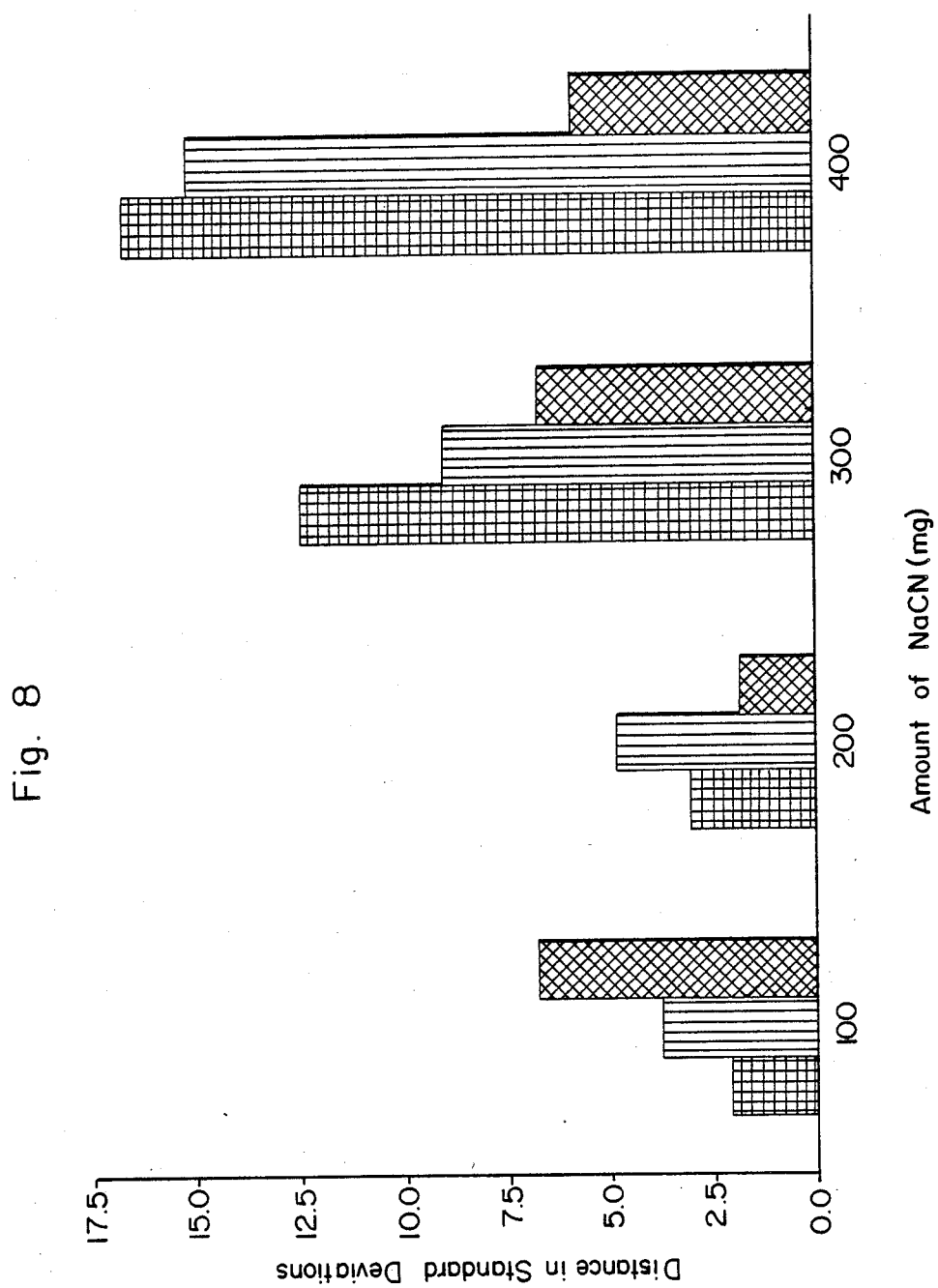

FIG. 8 shows DATRIL acetaminophen capsules analyzed with the colored end down in the reflector cone (white end up), containing approximately 100, 200, 300, and 400 milligrams of sodium cyanide packed in three configurations: in the colored end (#), in the white end (|||) and mixed throughout the capsule (XXX). The distance in standard deviations is given in terms of the training set of unadulterated DATRIL acetaminophen capsules in the direction of the sodium cyanide-containing capsule. The seemingly anomalous 100 milligrams "mixed" reading is probably the result of particle-size noise from, for instance, a large sodium cyanide crystal against the blue end of the capsule wall.

Figure 9:
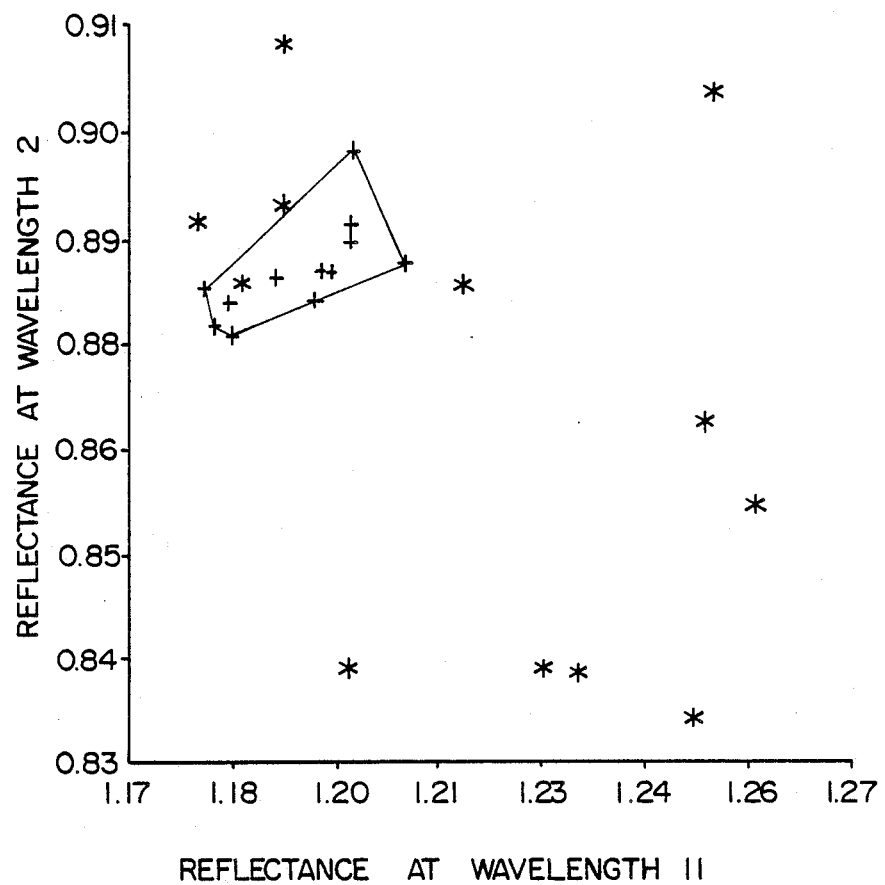

FIG. 9 shows one of six orthogonal views of a four-dimensional space formed by taking DATRIL-acetaminophen-capsule spectra at four wavelengths, for training-set capsules (+) and sodium cyanide-containing capsules (*). This figure shows the smallest convex polygon that can completely surround the training-set spectral points.

Figure 10:
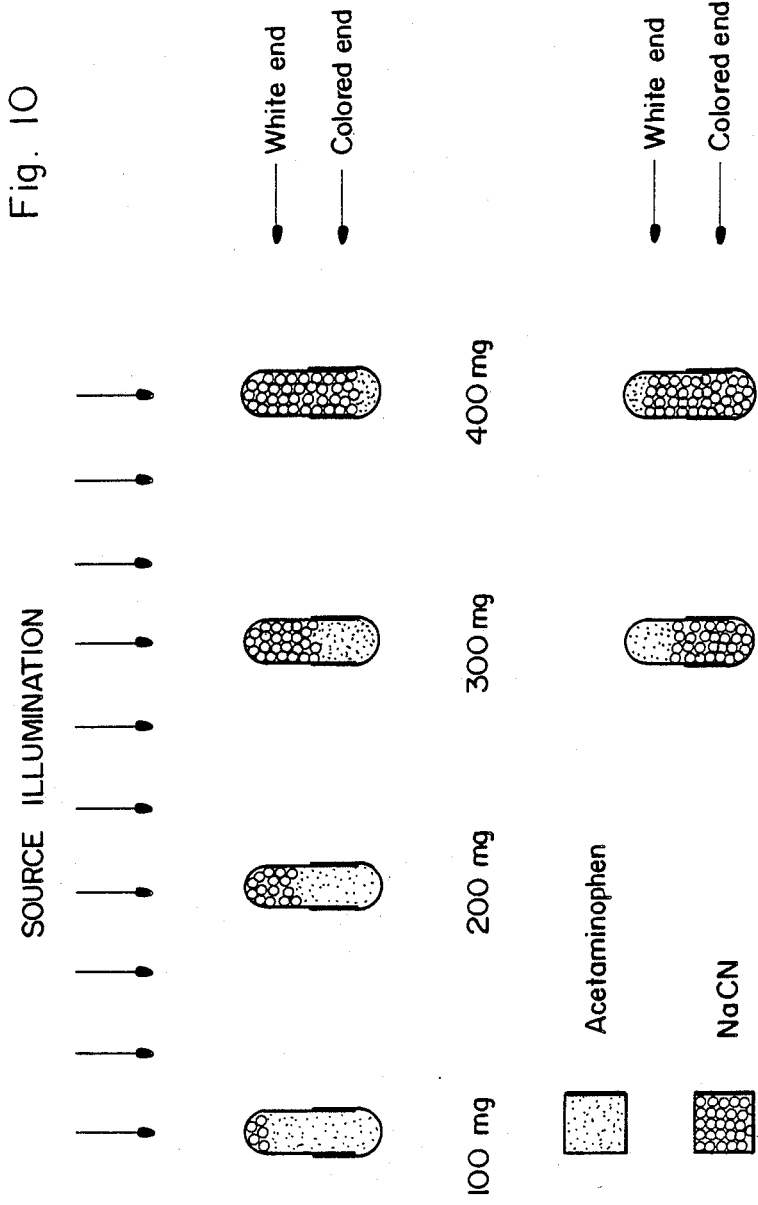

FIG. 10 shows the capsule orientation, the two different kinds of gelatin [scattering (white) and non-scattering (colored)] and the configuration of the contents of the capsule all affect the distance response (discrimination ability) of the BEAST for a given contaminant concentration. These factors can be used to advantage to provide additional information about the sample. The use of a conical reflector (positioned with the base of the cone perpendicular to the source illumination and with the vertex down toward the colored end of the capsules in this figure) permits spatial profiling of the capsule for an identified component.

Figure 11:
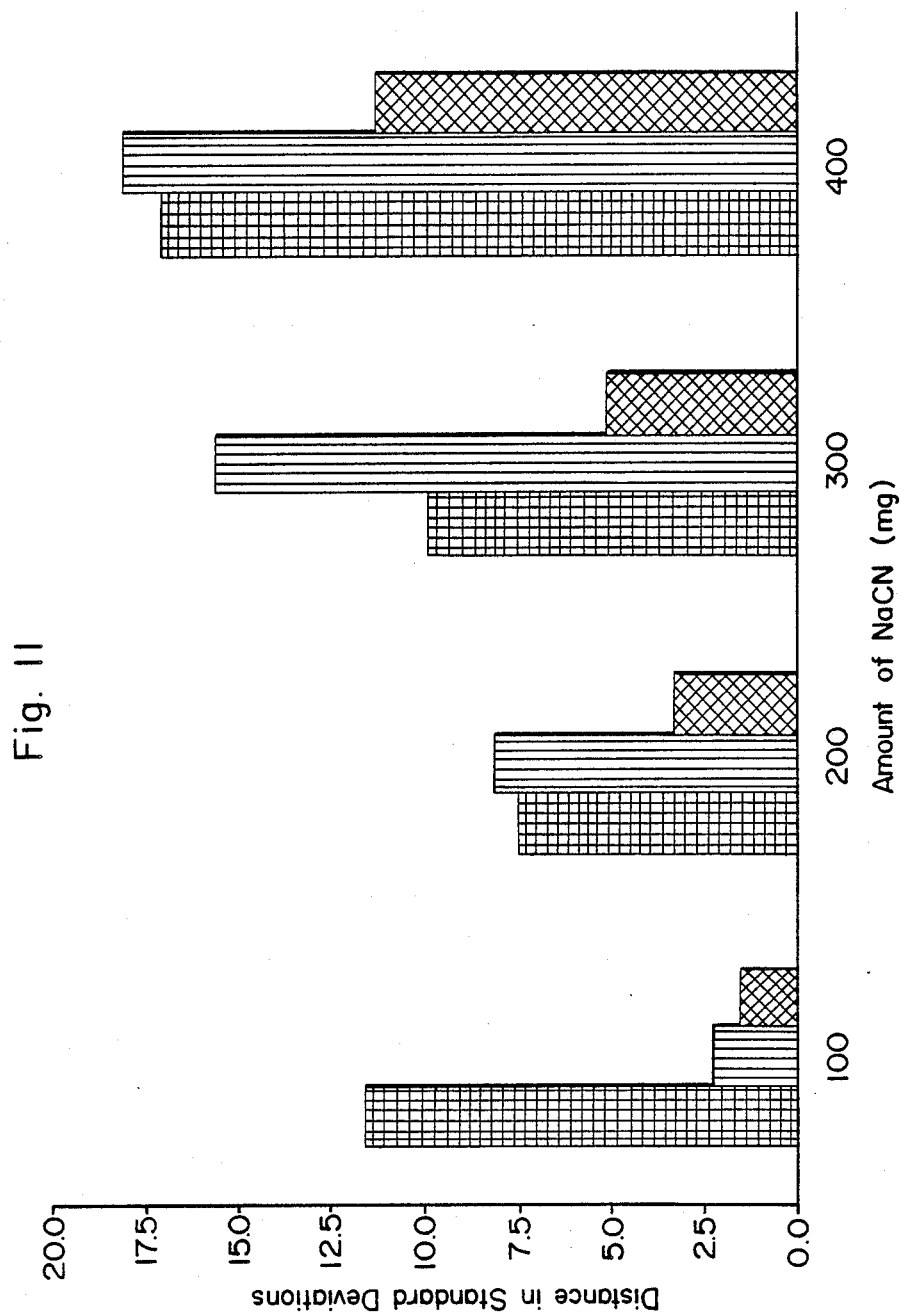

FIG. 11 shows ANACIN-3 acetaminophen capsules analyzed with the colored (blue) end up in the reflector cone, containing approximately 100, 200, 300 and 400 milligrams of sodium cyanide packed in three configurations: in the colored end (#), in the white end (|||) and mixed throughout the capsule (XXX).

Figure 12:
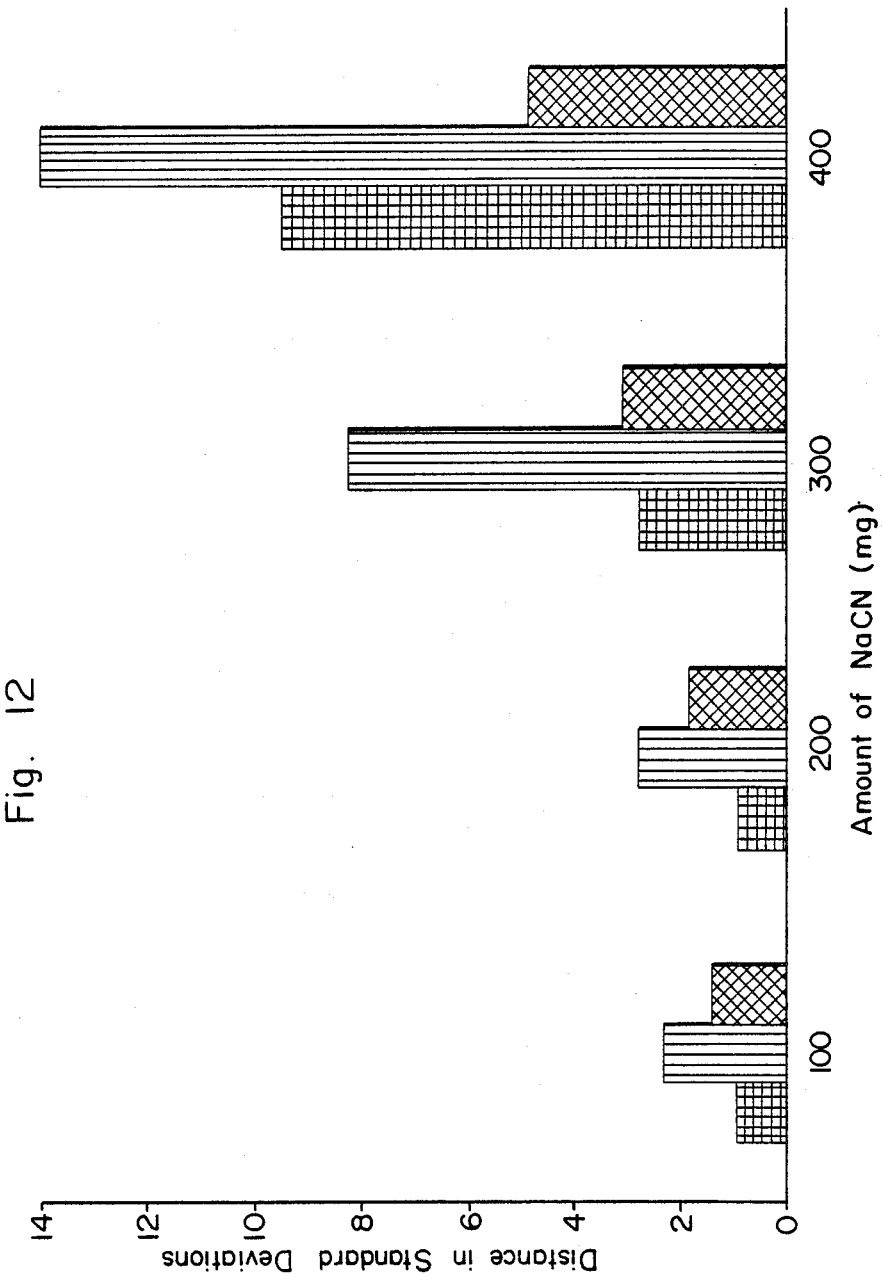

FIG. 12 shows ANACIN-3 acetaminophen capsules analyzed with the colored end down in the reflector conse (white end up), containing approximately 100, 200, 300 and 400 milligrams of sodium cyanide packed in three configurations: in the colored end (#), in the white end (|||) and mixed throughout the capsule (XXX).

Figure 13:
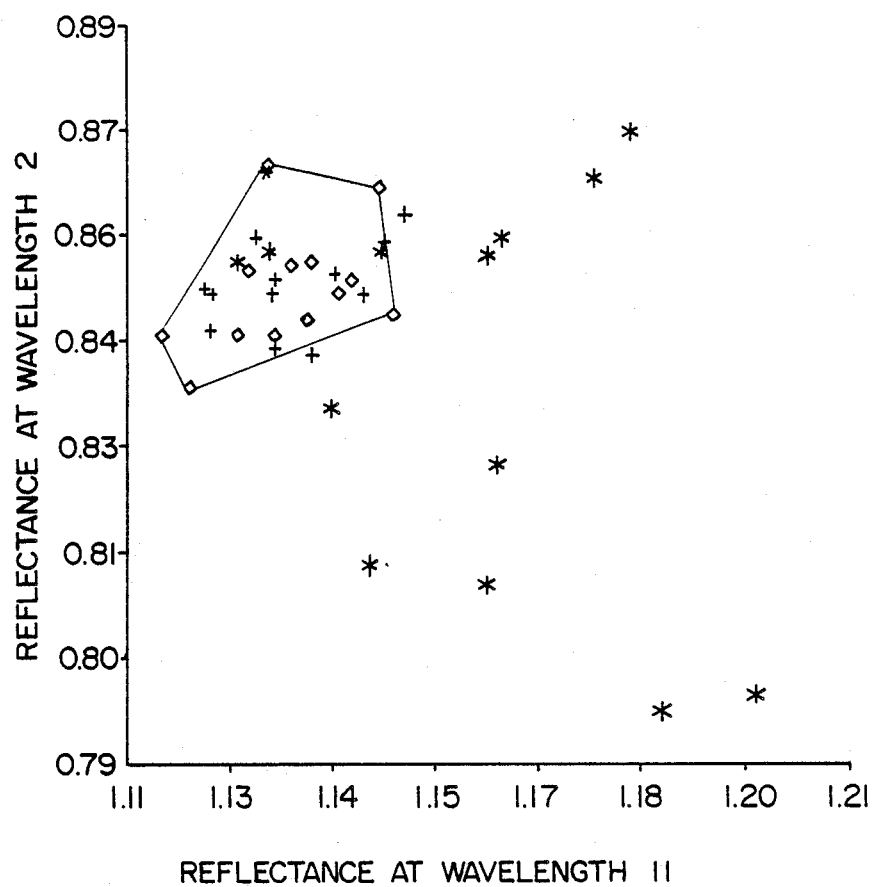

FIG. 13 shows one view of the four-dimensional space in which the ANACIN-3 acetaminophen capsules were analyzed. This figure corresponds to the DATRIL acetaminophen capsule FIG. 8. The smallest convex polygon containing all of the training-set capsules is shown and is larger than the corresponding DATRIL acetaminophen polygon. The difference in the size of the polygons is indicative of the greater variability of unadulterated ANACIN-3 acetaminophen capsules, a variability that is also reflected in the weight of the ANACIN-3 acetaminophen capsules compared to that of the DATRIL acetaminophen capsules.

FIG. 14 is a table of distances, in standard deviations, of spectral points of sodium cyanide-containing capsules from the training set cluster.

FIG. 15 is a table of distances, in standard deviations, of ANACIN-3 acetaminophen validation samples from the training set.

D. SUMMARY OF THE INVENTION

The foregoing objects, advantages and features of the present invention may be achieved with a method for detecting irregularities and inhomogeneities in samples, such as potassium cyanide or sodium cyanide in encapsulated drugs or tablets, using near-infrared reflectance spectroscopy in combination with a nonparametic clustering algorithm.

This method comprises the following steps. First, in order to construct a training set of homogeneous or unadulterated sample values, spectra of a set of samples of a particular known composition, such as a set of ANACIN analgesic capsules, are obtained at an appropriate number of discrete wavelengths using a near-infrared reflectance instrument. A transformation (i.e., mapping) is performed on each near-infrared ("NIR") spectrum of the training set so obtained. This transformation represents each n-wavelength spectrum as a single point in n-dimensional hyperspace, thus yielding a cluster of points in n-dimensional hyperspace for such samples (where n is the number of wavelengths used in constructing the training set). It will be understood by those of ordinary skill in the art that the prefix "hyper" as used in the present application generally designates a number, e.g., n, of dimensions; thus, "hyperspace" refers to a space of n dimensions, "hyperline" refers to a line in a hyperspace, and "hypercylinder" refers to a cylinder in a hyperspace. NIR spectra of a second set of samples of the same known composition, such as a second set of ANACIN analgesic capsules, are then obtained at the same wavelengths used for the training set samples. This second set of samples or validation sample set spectra are transformed to points in hyperspace in the same manner as the training set spectra. The data obtained from the validation sample set is used to validate the data obtained from the training set. In other words, if the points obtained from the spectra of the training set are valid, the points obtained from the spectra of the validation sample set will fall within the cluster of points obtained from the training set.

Samples are randomly selected from the training set samples to form a set of replicates of the training set. A Bootstrap Error-Adjusted Single-Sample Technique, using a Monte Carlo integration, is applied to training set sample replicates to approximate the hyperspace population-distribution or bootstrap replicate distribution of sample points from the training set. Next, a NIR spectrum is obtained for each inhomogeneous or adulterated sample and such a spectrum is transformed to a point in hyperspace. Confidence limits are then constructed on the training set using a univariate distribution of the training set sample replicates lying in the direction of the test-sample point. Using such limits, adulterated or inhomogeneous samples are indentified by noting those samples that fall more than three standard central 68% quantiles (or standard deviations) outside of the confidence limit. It will be understood by those of ordinary skill in the art that a "quantile" is generally the inverse of the integral of a function, normalized so that the total area under the function is between zero and unity, and that "three central 68% quantiles" is analogous, as described in more detail below, to three standard deviations of a one-dimensional normal distribution. An adulterated sample may then be identified by comparing the wavelengths and the quantile distances to those of known adulterants derived by the above procedure.

E. DETAILED DESCRIPTION OF THE INVENTION

1. Near Infrared Analysis

Near Infrared Reflectance Spectroscopy ("NIRS") is a rapid analytical technique for determining the composition of a selected sample. This technique uses the diffuse reflectance from a sample at several selected wavelengths to determine the sample's composition. Background and sample-matrix interferences are corrected automatically with NIRS through a computer-modeling process, thus permitting ordinarily difficult analyses to be easily made. The NIRS modeling process employs a "training set" of samples, the compositions of which are pre-determined by some other reliable chemical procedure, to "teach" the computer to recognize relationships between minute spectral features and sample composition.

The computer model developed in NIRS is composed of linear equations of the form:

$$\text{Concentration}(A) = C_o + \sum_{i=1}^{n} C_i R_i$$

where A is the sample component of interest (one equation is required for each component), n is the number of wavelengths at which spectra are obtained for the training set samples, $R_i$ is the reflectance at the i-th wavelength, and C represents a weighting coefficient determined through a multiple linear regression process. In other words, the NIRS model gives the sample composition from a number of linear equations, each of which expresses a particular component concentration as a weighted sum of the reflectances observed at a number of wavelengths.

Any instrument that generates near-infrared light of different wavelengths and quantitates its transmittance through a sample, or its reflectance from a sample, can be used to accomplish this near-infrared analysis. These instruments can be as simple as a filter photometer or as complex as a Fourier Transform Infrared Spectrophotometer. In addition, NIRS avoids the need for infrared instruments having a very large numbers of filters because of the broad spectral features and highly correlated wavelength vectors (i.e., $R_i$) obtained. Thus, relatively inexpensive instruments can be used for NIRS. Further, little or no sample preparation is required for NIRS; powders can be analyzed directly. Moreover, NIRS can be easily and profitably employed for quality control of samples, such as capsules and tablets and in the detection of adulterants placed in samples. It is advantageous to use NIRS for quality control because near-infrared radiation penetrates most compounds rather well, since the absorptions in the near-infrared region are generally weak.

There are, however, problems with the use of NIRS alone. It is not possible to identify all adulterants that might be placed in a particular product. The NIRS modeling process can only identify an adulterant, the spectra of which have been predetermined using NIRS, in a product for which training-set data have already been established. Therefore, in order to detect every adulterant in every type of product with ordinary NIRS, data for all types of products and all types of adulterants must be assembled.

2. The Bootstrap Error-Adjustment Single Sample Technique

The above problems with NIRS can be resolved by utilizing a new type of technique in conjunction with NIRS. This technique detects inhomogeneous or adulterated samples based on their near-infrared spectra. In addition, the use of such a technique in combination with NIRS would allow different multiple linear models (calibration equations) to be automatically applied to the analysis of fundamentally different samples. This technique, known as the Bootstrap Error-Adjusted Single-Sample Technique (the "BEAST"), provides more than a simple qualitative analysis of mixtures to determine whether a quantitative prediction equation applies to a particular sample. The BEAST also performs the following functions: (1) it detects any adulterated sample by determining that the adulterated sample is not similar to the previously analyzed unadulterated samples, (2) it qualitatively identifies the adulterant from a library of samples containing known adulterants, and (3) it provides a quantitative indication of the amount of adulterant present in the sample.

Figure 1:
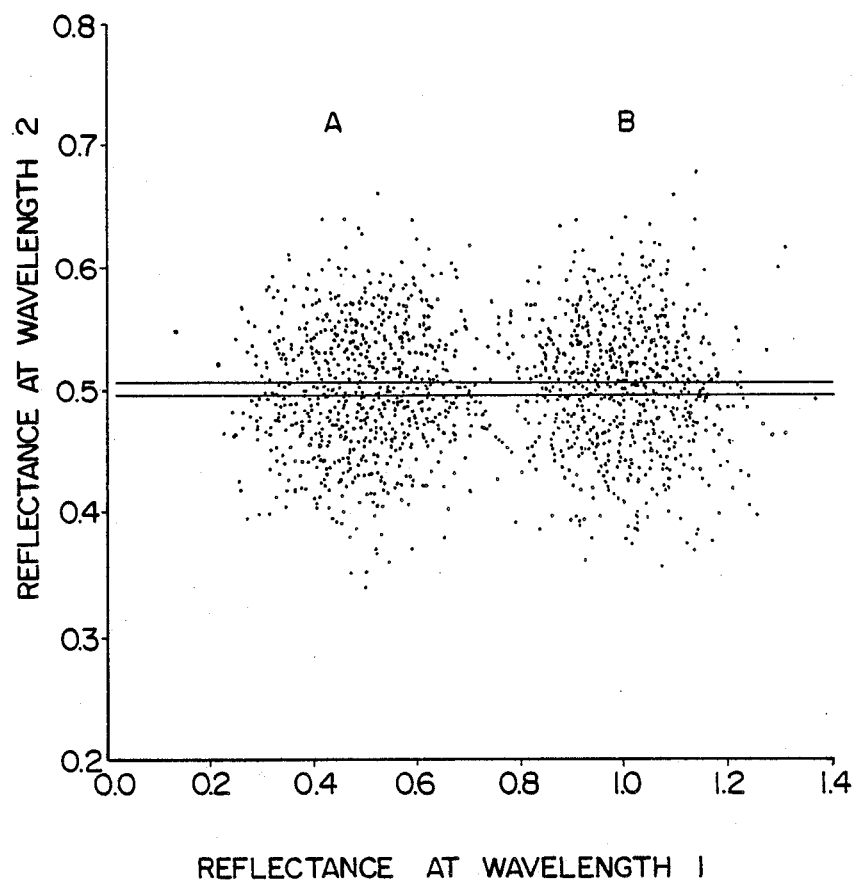

The BEAST solves the adulterated sample problem in the following manner. A sample is irradiated with near-infrared light and reflectance spectra are obtained at an appropriate number of wavelengths (at least two wavelengths are preferred, however the more wavelengths used the more accurate the BEAST potentially becomes). The BEAST then considers each of these monitored wavelengths to be a dimension in hyperspace. (Additional information vectors, like sample mass, density, etc. can also be added as more dimensions in hyperspace). For example, a spectrum of such a sample which is recorded at n wavelengths can be represented as a single point in n-dimensional hyperspace. This single point in hyperspace is translated from its origin in each dimension, by an amount that corresponds to the magnitude of the reflectance observed at each wavelength utilized. In this way, similar spectra yield points which appear in similar regions of hyperspace and the distribution of reflectances on each wavelength axis in hyperspace provides a projection of the clusters of similar points. (See FIG. 1) Unadulterated samples may be defined as samples, the transformed spectra of which, fall inside the cluster of points derived when the BEAST is trained with unadulterated training samples. Adulterated or contaminated samples are samples, the transformed spectra of which, fall outside that same cluster.

Confidence limits are set along any linear combination of wavelengths to define the surface of the cluster at a specified level. These confidence limits are obtained by using a bootstrap procedure to arrive at an estimate of the bootstrap replicate distribution based on the training-set distribution.

Figure 2:
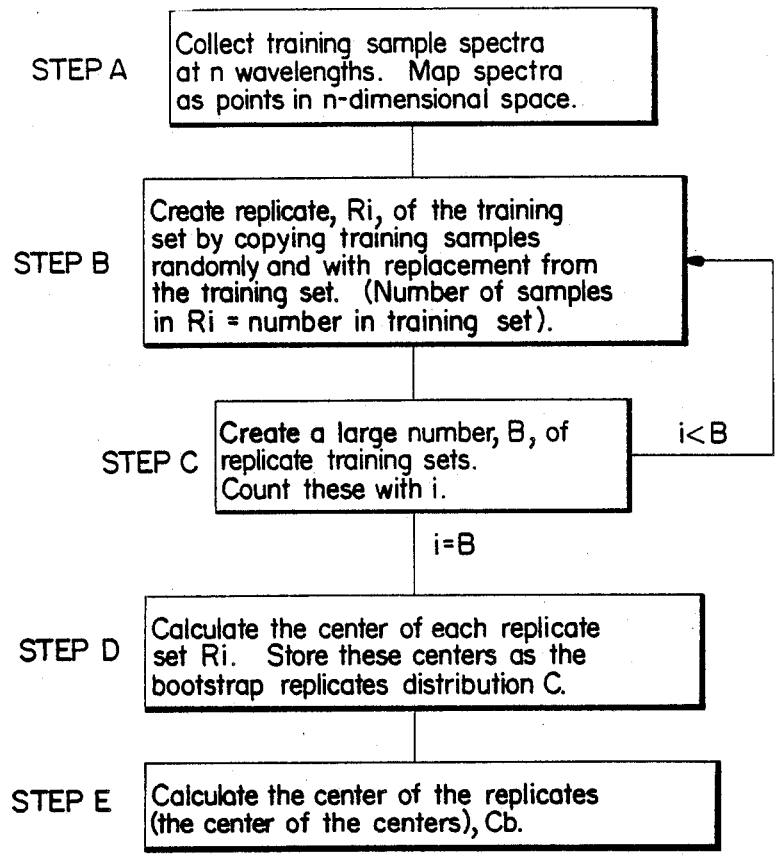
FIG. 2 is a flow diagram of the training process of the present invention.

The method of the present invention has the following basic steps:

1. A training set is carefully constructed from unadulterated samples in a fashion that captures all possible sample variance. (See FIG. 2, Step A) Fortunately, NIRS is predicated on the construction of such training sets, and a good deal of knowledge has been accumulated in this area. Spectra are then recorded and transformed or mapped to produce a set of points or a cluster of points in hyperspace. (See FIG. 2, Step A).

2. The reproducibility of the training set sample points is determined by obtaining the spectra of a second set of samples or validation set of samples (of the same composition as the training set) and transforming the spectra obtained into points in hyperspace. If those validation set sample points fall within the cluster of points obtained from the training set, the cluster of training set points has been validated.

3. A randomly selected set of samples (the same size as the training set) is chosen from the training set, with replacement from the training set, to form a second set of samples or the training set sample replicates. (See FIG. 2, Step B) A large number of these training set sample replicates are created by use of a Monte Carlo integration, as well established in the art. (See FIG. 2, Steps B and C) The training set sample replicates are analyzed by the same method used to analyze the training set samples.

4. The center of each training set sample replicate is determined by averaging all of the points obtained (or by finding the group mean). (See FIG. 2, Step D)

5. The centers of these training set sample replicates form a bootstrap replicate distribution, which may be superimposed on the hyperspace distribution of points of the training set samples. (See FIG. 2, Step D) The bootstrap replicate distribution is required for the subsequent analysis of adulterated samples. After the bootstrap replicate distribution is developed from the training set, the center of the bootstrap replicate distribution is determined by averaging all of the points. (See FIG. 2, Step E)

6. The spectrum of a test sample (such as an inhomogeneous or adulterated sample) is recorded and projected as a point into this hyperspace. (See FIG. 2, Step F)

Figure 3:
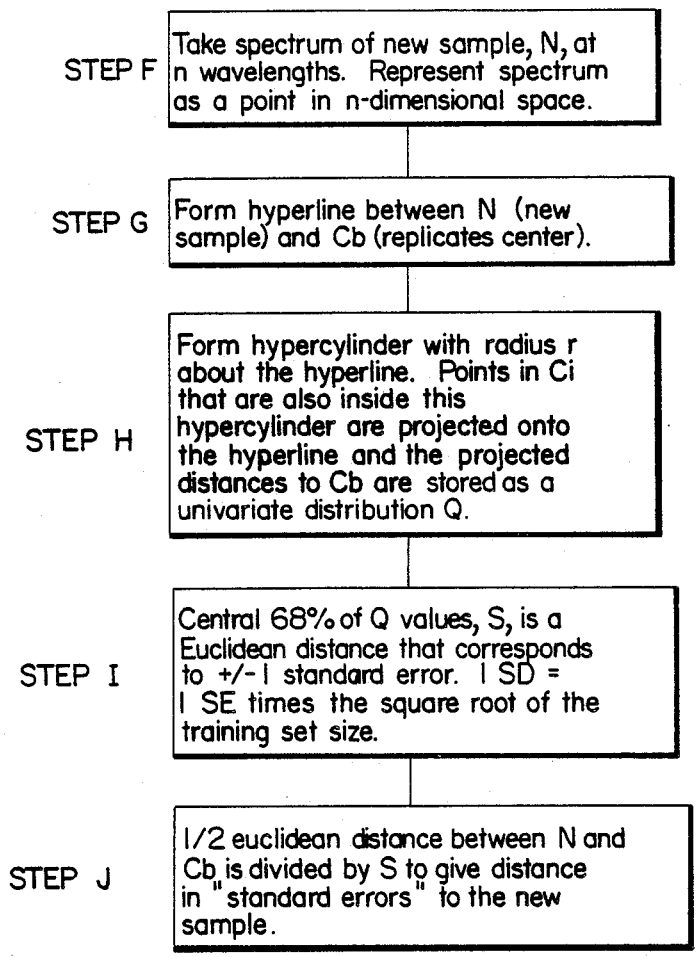
FIG. 3 is a flow diagram demonstrating how new or suspect samples are analyzed using the the method of the present invention.

7. A vector or hyperline is then formed in hyperspace between this test sample point and the computed center point of the bootstrap replicate distribution. (See FIG. 3, Step G)

8. Next, a hypercylinder is formed around this hyperline (the radius of the hypercylinder is typically 2 to 3 orders of magnitude smaller than its length). (See FIG. 3, Step H) This hypercylinder will contain a number of training set sample replicate points from the bootstrap replicate distribution (a minimum number of 50 points preferrably should be used).

9. The training set sample replicate points contained in the hypercylinder are projected onto the hyperline from anywhere in hyperspace by triangulation. (See FIG. 3, Step H) When the coordinates of these points are transformed into distances from the estimated center of the bootstrap replicate distribution, an univariate distribution is formed. (See FIG. 3, Step H)

10. This univariate distribution is used to construct confidence limits. The Euclidean distances between the center of the bootstrap replicate distribution and the points in the hypercylinder are sorted, and the central 68% of the values is measured. This Euclidean distance represents twice the standard error. (See FIG. 3, Step I) A standard deviation (SD) is then calculated by multiplying one-half of central 68% of the sorted distances by the square root of the number of samples used in constructing the training set. (See FIG. 2, Step I). The distance in standard deviations to the test sample point may then be calculated. (See FIG. 3, Step J)

The reliance of the BEAST on nonparametric techniques (techniques that assume no particular underlying distribution) produces an analytical method that functions without assumptions about the shape, size, symmetry or orientation of spectral-point clusters in hyperspace. This freedom is important because cluster characteristics have been shown to be unpredictable. The BEAST, thus, can be used both for quality control applications (i.e., to identify empty capsules, or rust, metal shavings or other contaminants in capsules) and for identification of adulterants placed in capsules (i.e., where a capsule has been the subject of deliberate tampering). Under such widely varying conditions, the unpredictability of the cluster characteristics makes the use of nonparametric techniques even more significant.

3. Experimental Procedure—Analysis of Capsules

Three brands of capsules were analyzed using the above described method: HOOK'S COLD CAPS brand capsules (Hook's Drugs, Inc., Indianapolis, IN) containing phenylpropanolamine hydrochloride and chlorpheniramine maleate; EXTRA STRENGTH DATRIL brand capsules (Bristol Meyers Co., New York, NY) containing acetaminophen [N-(4-Hydroxylphenyl)acetamide]; and MAXIMUM STRENGTH ANACIN-3 brand capsules (White Hall Laboratories, Inc., New York, NY) containing acetaminophen.

The adulterants used in these experiments were: (1) Ferric Oxide, reagent grade (J. T. Baker Chemical Company, Phillipsburg, NJ); (2) Aluminum metal, 20 mesh (Fisher Scientific, Fairlawn, NJ); (3) Arsenic trioxide, reagent grade (Fisher Scientific); (4) Sodium fluoride, reagent grade (MCB, Norwood, OH); (5) Crystalline sodium cyanide, reagent grade (Aldrich Chemical Company, Milwaukee, WI); and (6) Granular potassium cyanide, reagent grade (Mallinckrodt, Paris, KY). The amount of these contaminants used were varied from lethal doses to smaller nonlethal doses.

All adulterants were added to the capsules on an "as is" basis without any grinding, sifting or sample preparation. The cyanide was removed from the reagent container and kept covered to reduce the absorption of water. Capsules were filled with cyanide from this covered reservoir, but no additional steps were taken to control water absorption.

Spectral data for all experiments were collected at 18 discrete wavelengths by a Technicon Instruments Corps. INFRAALYZER 400 filter spectrophotometer connected to a VAX 11/780 computer (Digital Equipment Corporation) with custom interface, graphics and database-management programs. These programs, and the BEAST, were written in SPEAKEASY IV DELTA language (VMS version, Speakeasy Computing Corporation, Chicago, IL) and VAX 11 BASIC language (Version 2.4).

Reproducible positioning of capsules is important and minimizes the error of repeated readings of the individual capsules. Therefore, HOOK'S COLD CAPS brand capsule samples were analyzed by placing the capsules into an elliptically-shaped aluminum reflector (#1468 Progressus Company, Freeport, NY). Reproducible positioning of the capsules within the reflector was achieved by removing the "blister" from a HOOK'S COLD CAPS brand capsule "blister-pack," trimming it to about two (2) millimeters in height and gluing it into the center of the reflector with the open side up.

DATRIL acetaminophen and ANACIN-3 acetaminophen capsule samples were analyzed by placing them in a substantially 90° conical holder or reflector as described in copending application Ser. No. 07/165,751 filed on March 9, 1988 and as incorporated herein by reference. A nichrome wire support was used to achieve reproducible upright vertical capsule positioning within the cone. Optical surfaces of both reflectors were polished with a cemical polishing paste.

OBTAINING THE TRAINING SET VALUES USING THE BEAST

Each of the following experiments began with an analysis of 10–13 unadulterated capsules in order to train the BEAST to recognize a "good" (i.e., unadulterated) capsule. The training process was then tested by using the BEAST to measure the distance, in standard deviations, of the same number (10–13, depending upon the capsule brand) of "good" capsules from the center or mean of the training-sample cluster. The surface of a cluster was defined as being three standard deviations ("SDs") away from its center or mean. In theory, then, all of the "good" test capsules should appear less than three SDs from the training-set center, while all of the "bad" (i.e., contaminated) capsules should appear more than three (3) SDs from the training-set center.

A training set composed of ten capsules produces a total of 92378 possible training set sample replicates (calculated from 2n-1 combinations of n points, taken n at a time with replacement from the training set). Calculation of 1000 training set sample replicates represents more than one percent (1%) of the possible bootstrap replicate distribution, a greater proportion of the distribution than is usually covered by Monte Carlo integration techniques. A compromise between coverage and execution time must be reached in using the BEAST; therefore, 1000 training set sample replicates were used for all the foregoing capsule experiments. This resulted in a BEAST analysis time of about four seconds per capsule. A BEAST optimized for quality control would be even faster. Although a training set sample size of about ten capsules is rather small, the variability from unadulterated capsule to capsule is small and thus ten capsules should constitute a sufficient training set. Nonetheless, as the variability of the mixtures in the training set increases, the number of training set samples required by the BEAST also increases. This is a common requirement in NIRS techniques.

In determining the training set sample values, the hypercylinder radius was set at 0.00060. This value was selected in order to ensure that there were a sufficient number of points in the hypercylinder to set appropriate confidence limits. This value has the same dimensions as the log (1/R) values collected by the spectrophotometer. Reproducibility of BEAST distances is a function of the number of training set sample replicates employed, the hypercylinder radius, and the training set utilized. The parameters given above (and used to obtain all of the experimental results) have been found to give relative standard deviations of approximately seven percent (7%).

EXAMPLE I

Ten HOOK'S COLD CAPS brand capsules were analyzed using NIRS at two discrete wavelengths. These ten cold capsules were used to construct a training set. It was assured that standard capsules with the least uniformity were adequately represented in the training set. This was done by selecting those capsules, the spectra of which, yielded points in hyperspace furthest from the center of the training set sample cluster. The net effect of this procedure is to make the training-set cluster in hyperspace larger, and the distances measured in hyperspace in SDs smaller. Although this procedure increases the likelihood that all unadulterated capsules will test as "good" or unadulterated, it also makes it more likely that adulterated samples will also test as "good" or unadulterated. This however, is a problem only if adulterated samples are spectroscopically very similar to the unadulterated samples. (Such similarity was not observed in any of these experiments.) The most likely effect of expanding the limits of the training set with extreme examples of unadulterated capsules is the raising of the detection limit for some adulterants. The importance of this possibility will be examined below.

Ten additional cold capsules were analyzed using NIRS at the same two wavelengths. These cold capsules constituted a second set or validation set of samples. The distances of these points, in standard deviations, from the center of the hyperspace cluster of points yielded from spectra of the training-sample samples are as follows: 0.30, 0.69, 0.42, 0.38, 0.85, 0.70, 0.33, 0.58, 0.23, 0.84. These cold capsules serve to validate the results of the training process. The fact that all of these distances are less than one standard deviation indicates that the BEAST is unlikely to reject an unadulterated capsule accidentally.

After the above values were determined twenty-one HOOK'S COLD CAPS brand capsules were tested for adulterants using the method of the invention. (Twenty capsules were filled and one capsule was empty) FIG. 4 provides the distances of the points (in SDs) yielded from the spectra of these twenty-one HOOK'S COLD CAPS brand capsules from the center of the training-set cluster. FIG. 4 shows that adulterants were found in these HOOK'S COLD CAPS brand capsules. For all twenty-one capsules, these distances exceeded the three SD limit set as the dividing line between "good" or unadulterated and "bad" or adulterated capsules. The results indicate that a variety of adulterants can be detected in intact capsules by using only two near infrared wavelengths and a simple reflector-based capsule mount. Aluminum shavings are clearly detectable inside the capsule even though the reflector is also aluminum. A completely empty capsule can be easily differentiated from a capsule contaminated with aluminum. The BEAST algorithm works by detecting the absence of components that should be present as well as by detecting the presence of components that should be absent. This type of functioning gives the BEAST a powerful ability to detect all kinds of tampering. Presumably it is the absence of cold remedy, combined with the added scattering of specular radiation from the aluminum shavings inside the capsule, that produces the difference between the aluminum-containing capsules and the cold remedy that is measured by the BEAST.

EXAMPLE II

Training set samples of DATRIL acetaminophen were analyzed using NIRS. A bootstrap replicate distribution was obtained and the training set was validated. Next, four DATRIL acetaminophen capsules containing 93, 218, 289 and 383 milligrams of sodium cyanide were tested using the substantially 90° conical reflector as described in copending application Ser. No.

07/165,751 and as incorporated herein by reference. The cyanide was packed into the white end of the capsule, which was oriented toward the vertex (bottom) of the conical reflector. FIG. 5 provides the results of this test. The slight differences between the theoretical and observed values can probably be attributed principally to two factors:

1. the thickness and opacity of the capsule itself are not constant from one end to the other (for instance, there are two layers of gelatin in the middle of the capsule); and 2. peculiarities are introduced into the capsule spectra, and therefore into the distances in SDs, by the particular orientations that the capsule contents (both sodium cyanide and acetaminophen crystals) assume in a single capsule packing.

Knowledge of the characteristics of the conical reflector permits some spatial profiling of the capsule for a given adulterant. A specific BEAST response can indicate either a relatively large amount of adulterant in the lower sections of the capsule or a relatively small amount of adulterant in the higher sections. This classic dilemma—that of too many unknowns and too few equations—is solved simply by inverting the capsule and running the BEAST again. The total amount of adulterant in the capsule is obtained by developing ordinary NIRS calibrations using homogeneous training sets (containing only one type of capsule configuration).

EXAMPLE III

The most important feature of the conical reflector is its ability to discriminate between capsules with similar component concentrations. This ability is demonstrated by an experiment conducted with four tainted DATRIL acetaminophen capsules. Capsules 1 and 2 contained about 170 milligrams of sodium cyanide, while capsules 3 and 4 contained about 460 milligrams of sodium cyanide. The remainder of each capsule was composed of he acetaminophen powder normally found in the capsules, giving an average total capsule mass of about 600 milligrams. Data were collected at four discrete wavelengths with both the elliptical and conical reflectors, and the Euclidean distances among the spectra of the four capsules was determined.

The reflector with the greatest discriminating capability maximizes the average distance ratio:

$$\frac{\text{distance between spectra of dissimilar capsules}}{\text{distance between spectra of similar capsules}}$$

This ratio was calculated for each reflector using all possible combinations of the four capsules. The average ratio was only 3.83 using the elliptical reflector, but climbed to 10.53 for the same capsules using the cone. These results indicate that the conical reflector is more sensitive to slight differences in capsule composition, probably because less specular reflectance (from the reflector and the surface of the capsule) reaches the detector using this corner-reflector configuration.

Spectroscopically, the ends of most capsules are not equivalent. In ANACIN acetaminophen and DATRIL acetaminophen, the shorter end of the gelatin capsule is brightly colored (blue in ANACIN-3 acetaminophen and green in DATRIL acetaminophen) while the longer end is white and contains a light-scattering medium. FIG. 6 shows the training, validation, and sodium cyanide-containing sample sets for ANACIN-3 acetaminophen in a two-wavelength space. The two distinct training set sample clusters and the two distinct validation set sample clusters are the result of including both of the possible oreintations of ANACIN-3 acetaminophen in the conical reflector (colored end up and colored end down) in the plot. It is interesting to note that the corresponding training set and validation set clusters are not necessarily the same size or shape, even though the same capsules were used in each and only the capsule oreintation in the cone had changed. In addition, the major axes of the sodium cyanide-containing clusters are approximately perpendicular to those of the training set and validation set samples. These facts demonstrate that the size, shape and directional orientation of spectral clusters in space are not predictable a priori. This unpredictability, in turn, violates basic assumptions of oher qualitative NIRA techniques, making their use in many applications somewhat suspect.

EXAMPLE IV

DATRIL acetaminophen capsules containing approximately 100, 200, 300 and 400 milligrams of sodium cyanide and in three configurations (sodium cyanide packed in the colored end of the capsule, in the white end, and mixed into the acetaminophen throughout the capsule) were analyzed at four discrete wavelengths by means of the same conical reflector as used in Example II. The purpose of this experiment was to determine the BEAST distance response (in SDs) for different amounts of adulterants in various locations throughout a capsule. The results are summarized in FIGS. 7 and 8. The data in FIG. 7 were collected with the colored end of the capsule up in the cone-shaped receptacle of the reflector, whereas the data in FIG. 8 were collected with the colored end of the capsule down. In general, the distances in SDs measured from the training-set spectra to those of the adulterated capsules are greater when the colored ends of the capsule are up in the cone-shaped receptacle of the reflector. The Euclidean distances, however, are about the same for both capsule orientations. The distance in SDs varies because the BEAST scales the Euclidean distance with the probability of the point lying in its particular direction, and the training-set cluster size (probability) is larger when capsules are measured with their white ends pointing up in the reflector cone.

FIG. 9 shows one of six orthogonal views of the four-dimensional wavelength space in which the DATRIL acetaminophen capsules were analyzed. The FIG. 9 data were obtained with the colored end of the capsule up. The corresponding colored-end-down views are similar; however, the training-set cluster is slightly larger and the distances to the adulterated samples are slightly smaller. The net effect of these changes is to reduce the sensitivity of NIRS and the BEAST when measurements are taken through the white end of the capsule (i.e., with the colored end down in the cone). This result is predictable because NIRS gives information about particle size as well as about the chemical contents of a capsule; the particle-size information is obscured somewhat by the light-scattering medium in the white end of the capsule.

FIG. 8 demonstrates further the effect of taking the capsule-contents spectrum through two different layers of gelatin. An examination of the data for the 100 and 200 milligram samples shows that packing these amounts of sodium cyanide in the white end of the capsule produces greater discrimination (in SDs) than packing them in the colored end. However, packing 300 and 400 milligrams of sodium cyanide into the white end produces a smaller response than packing the same amount in the colored end. The reason that this reversal is observed is simply that the colored end allows more information about the capsule contents to pass through: when 100 and 200 milligrams of sodium cyanide are in the white end, essentially all of the sample reflectance reaching the detector passes through the white end. However, when 300 and 400 milligrams of sodium cyanide are packed into the capsule, the capsule is more than half full and a significant amount of the diffuse reflectance is able to reach the detector on the NIRS instrument through the white end as well as the colored end even when the sodium cyanide is packed into the colored end. (See FIG. 10) Unadulterated capsules are generally completely full of acetaminophen and typically some must be removed in order to add an adulterant. The ability to ascertain the profile of the distribution of an adulterant in a capsule might provide useful forensic evidence because there is more than one way to introduce an adulterant into a capsule. The distribution profile has obvious applications in quality control as well.

EXAMPLE V

Profiling experiments were also conducted with ANACIN-3 acetaminophen capsules using sodium cyanide as an adulterant. Training set data was obtained and a bootstrap replicate distribution determined. As with the DATRIL acetaminophen capsules, approximately 100, 200, 300 and 400 milligrams of sodium cyanide were placed in the capsule in three configurations (packed toward the colored end, toward the white end, and mixed throughout the capsule). The results appear in FIGS. 11 and 12. For ANACIN-3 acetaminophen, the colored end (blue) of the capsule might absorb more in the near-infrared, relative to the white end, than the colored end of a DATRIL acetaminophen capsule (green). The ratio of the scale maxima of the figures for DATRIL acetaminophen (FIG. 7: FIG. 8) is 40:17 or 2.29:1, while the same ratio for ANACIN-3 acetaminophen is 20:14 or only 1.43:1 (FIG. 11: FIG. 12). The difference in these ratios indicates that it is more difficult to measure the contents of an ANACIN-3 acetaminophen capsule through the colored end than it is to measure the contents of a DATRIL acetaminophen capsule through the colored end. Another explanation for the reduced ability of NIRS to read through the colored end of the ANACIN-3 acetaminophen capsule is based on the contents of the capsules. In fact, there is a noticeable difference in the consistency of unadulterated powder from a DATRIL acetaminophen and an ANACIN-3 acetaminophen capsule. ANACIN-3 acetaminophen seemed to consist of larger flakes than DATRIL acetaminophen, and also had a greater tendency to adhere to the walls of the capsule, in spite of attempts to empty it. The amount of powder remaining in the capsules after they were emptied (but, just before they were repacked) was not measured, and it is quite possible that this amount was significantly larger in the ANACIN-3 acetaminophen capsules than it was in the DATRIL acetaminophen product. Special attempts were not made to remove this clinging powder because a tamperer would probably not make such attempts. "Screening" of the adulterant by the acetaminophen powder could therefore be a significant factor in the ANACIN-3 acetaminophen results observed.

Overall, the differences (SD distances) between the adulterated capsules and the training set are smaller for ANACIN-3 acetaminophen than they are for DATRIL acetaminophen. The immediate reason is that the ANACIN-3 acetaminophen training-set hyperspace cluster itself is larger than the hyperspace cluster for the DATRIL acetaminophen training set, relative to the adulterated samples (compare FIG. 13 for ANACIN-3 acetaminophen to the corresponding DATRIL acetaminophen FIG. 9). The fact that the ANACIN-3 acetaminophen training-set hyperspace cluster is larger indicates that ANACIN acetaminophen capsules are normally more variable in their contents than DATRIL acetaminophen capsules—a fact confirmed by weighing the capsules in each training set. The mean mass of the DATRIL acetaminophen capsules was 695 milligrams, with a standard deviation of 5.5 milligrams. The mean of the ANACIN-3 acetaminophen capsules was 670 milligrams with a standard deviation of 19.2 milligrams. Samples of ANACIN-3 acetaminophen capsules are therefore about 3.5 times more variable than DATRIL acetaminophen capsules, making the detection of any kind of adulteration in ANACIN acetaminophen a more difficult proposition than the corresponding determination in DATRIL acetaminophen. Nevertheless, the fact that the BEAST responds to the absence of components that should be present as well as to the presence of contaminants that should not be in the sample makes the detection of adulteration possible under less-than-ideal conditions.

FIG. 14 gives BEAST distances in SDs for sodium cyanide contaminated DATRIL acetaminophen and ANACIN-3 acetaminophen capsules. Both capsule orientations (colored end up and colored end down) were checked and the larger of the two discrimination values appears in the FIG. 14. (Process-control applications ordinarily use the larger of the two values) When the commonly used limit of 3 SDs is applied to the training-set cluster, it is apparent that all of the adulterated DATRIL acetaminophen capsules could be detected and rejected. All but two of the adulterated ANACIN-3 acetaminophen capsules are also rejected when only four wavelengths are used. The two ANACIN-3 acetaminophen capsules that were not rejected had the lowest sodium cyanide concentrations and were placed in the most unfavorable configurations.

The fundamentally nonparametric character of the BEAST permits information vectors other than near-infrared wavelengths to be used directly in the calculations as though these vectors were near-infrared wavelengths. For example, the retention time of a substance in a liquid chromatography (LC) experiment could be added to the near-infrared wavelength reflectance data from n wavelengths to produce a BEAST analysis in the (n+1)-dimensional space created by the addition of the retention time. Distributional assumptions of normality are often hard enough to justify when only near-infrared wavelengths are used, and the addition of dissimilar information only makes these assumptions more difficult to justify. The performance of the BEAST, being free of assumptions regarding data distributions, should prove to be even more superior to parametric methods in such applications. The current proliferation of laboratory information management systems makes a wealth of information available to investigators, most of which might be profitably used with the BEAST.

In order to demonstrate this flexibility of the BEAST the total masses of the ANACIN-3 acetaminophen training-set capsules were added to the training-set points in hyperspace. Capsule mass is an important parameter because, in unadulterated capsules, this variable is tightly controlled. In addition, the weighing of capsules is one of the few tasks that can be performed more rapidly than NIRS. Of course, capsule weight is not in itself a sufficient indicator of tampering. For example, unadulterated DATRIL acetaminophen capsules weighed 694 milligrams (SD=5.5 milligrams), whereas the sodium cyanide contaminated capsules weighed 711 milligrams (SD=61.5 milligrams). Accordingly, a substantial portion of tainted DATRIL acetaminophen capsules would pass a test based on weight information alone.

The last group of ANACIN-3 acetaminophen distances in FIG. 14 represents the same set of capsules that produced the 4-D-space distances, except that the total mass of each capsule was included to create a 5-D space. The BEAST was then retrained by adding the total capsule mass also to each training set sample. The addition of the mass information is enough to allow the BEAST to correctly identify every sodium cyanide containing capsule as being tainted.

Control, or validation, samples (unadulterated ANACIN-3 acetaminophen capsules that were not used in the training set) are also correctly identified in every case (both with and without the weight information) as being untainted (see FIG. 15). Unlike the situation for HOOK'S COLD CAPS brand capsules discussed earlier, the unadulterated ANACIN-3 acetaminophen capsules were intentionally divided randomly into training and validation sets. The only precaution taken in constructing these sets was to make sure that both sets contained approximately equal numbers of capsules with total masses below and above the mean capsule mass. The more random nature of this selection process increases the distance in SDs of the validation capsules from the training set. As shown in FIG. 14, the higher value of the two possible capsule orientations (colored end up and colored end down) has been calculated.

EXAMPLE V

Potassium cyanide is perhaps the most common highly toxic adulterant added to over-the-counter drugs. The detection limit for potassium cyanide under optimal conditions in over-the-counter capsules is thus of great interest. Potassium cyanide was packed into the colored end of eight ANACIN-3 acetaminophen capsules, over a range of concentrations from 1 to 87% (by weight). A strong functional relationship exists between the concentration of potassium cyanide in the capsules and the distance of the capsule (in SDs) from the training set determined by the BEAST. This relationship suggests that the BEAST might be directly useful as a system or process control technique when:

1. the system is defined by one or more monitored variables (such as the wavelengths in this experiment);
2. the BEAST can be trained to recognize a "normal" state as described by typical variations of the monitored variables (in the same way that the BEAST was trained by using a set of unadulterated capsules in the present experiment); and
3. a given BEAST distance response in a particular direction can be functionally related back to a parameter of interest in the system (as the quadratic response of the reflector cone can be used to predict the location and amount of a contaminant in a capsule).

The ease with which the BEAST problem can be restructured into a form readily solvable by parallel-processing techniques might soon make real-time control with the BEAST an effortlessly attainable goal.

The potassium cyanide 3-SD detection limit calculated from the eight ANACIN-3 acetaminophen capsules is 2.6 milligrams (less than 0.4% of the typical weight of an ANACIN-3 acetaminophen capsule). The smallest amount of potassium cyanide placed in these capsules, 9 milligrams, caused the capsule in which it was placed to appear 5.96 SDs from the training set in 4-D (4-wavelength) space.

While the foregoing has been described with respect to preferred embodiments and alternatives thereto, they are not intended nor should they be construed as limitations on the invention. As one skilled in the art would understand many variations and modifications of these embodiments may be made which fall within the spirit and scope of this invention.

What is claimed:

1. An analytical method for detecting adulterants in samples using a Near Infrared Reflectance Analysis (NIRS) instrument comprising the steps of:
    (a) obtaining spectra at an appropriate number of wavelengths for a training set of an appropriate number of unadulterated samples;
    (b) performing a transformation of each spectrum by representing such spectrum as a single point in hyperspace, and thus yielding a cluster of points in n-dimensional hyperspace, where n is the number of wavelengths utilized;
    (c) creating a large set of training set sample replicates, each replicate being the same size as the training set, by randomly selecting samples from the training set, with replacement from the training set, and thus creating a bootstrap replicate distribution;
    (d) calculating the center of the bootstrap replicate distribution;
    (e) obtaining a spectrum for an adulterated sample;
    (f) transforming this spectrum into a point in hyperspace;
    (g) forming a hyperline in hyperspace between the point in hyperspace yielded from the spectrum of the adulterated sample and the center point of the bootstrap replicate distribution;
    (h) forming a hypercylinder around the hyperline containing points of the training set sample replicates;
    (i) projecting the multivariate points of the training set sample replicates onto the hyperline to form a univariate distribution of points;
    (j) using this univariate distribution of points to construct confidence limits;
    (k) identifying as abnormal the adulterated sample, the point of which falls three central 68% quantiles outside of the cluster of points yielded by the replicate spectra obtained from the training set sample replicates of the training set.

2. An analytical method for detecting inhomogeneous samples using a Near Infrared Reflectance Analysis (NIRS) instrument comprising the steps of:
    (a) obtaining spectra at an appropriate number of wavelengths for a training set of an appropriate number of homogeneous samples;
    (b) performing a transformation of each spectrum by representing such spectrum as a single point in hyperspace, and thus yielding a cluster of points in n-dimensional hyperspace, where n is the number of wavelengths utilized;

(c) creating a large set of training set sample replicates, each replicate being the same size as the training set, by randomly selecting samples from the training set, with replacement from the training set, and thus creating a bootstrap replicate distribution;

(d) calculating the center of the bootstrap replicate distribution;

(e) obtaining a spectrum for an inhomogeneous sample;

(f) transforming this spectrum into a point in hyperspace;

(g) forming a hyperline in hyperspace between the point in hyperspace yielded from the spectrum of the inhomogeneous sample and the center point of the bootstrap replicate distribution;

(h) forming a hypercylinder around the hyperline containing points of the training set sample replicates;

(i) projecting the multivariate points of the training set sample replicates onto the hyperline to form a univariate distribution of points;

(j) using this univariate distribution of points to construct confidence limits;

(k) identifying as abnormal the inhomogeneous sample, the point of which falls three central 68% quantiles outside of the cluster of points yielded by the replicate spectra obtained from the training set sample replicates of the training set.

3. An analytical method for detecting adulterants using a Near Infrared Reflectance Analysis (NIRS) instrument comprising the steps of:

(a) obtaining spectra at an appropriate number of wavelengths for a training set of an appropriate number of adulterated samples;

(b) performing a transformation of each spectrum by representing such spectrum as a single point in hyperspace, and thus yielding a cluster of points in n-dimensional hyperspace, where n is the number of wavelengths utilized;

(c) creating a large set of training set sample replicates using a Monte Carlo integration, each replicate being the same size as the training set, by randomly selecting samples from the training set, with replacement from the training set, and thus creating a bootstrap replicate distribution;

(d) calculating the center of the bootstrap replicate distribution;

(e) obtaining a spectrum for an adulterated sample;

(f) transforming this spectrum into a point in hyperspace;

(g) forming a hyperline in hyperspace between the point in hyperspace yielded from the spectrum of the adulterated sample and the center point of the bootstrap replicate distribution;

(h) forming a hypercylinder, the radius of which is 2 orders of magnitude greater than the length, around the hyperline containing points of the training set sample replicates;

(i) projecting the multivariate points of the training set sample replicates by triangulation onto the hyperline to form a univariate distribution of points;

(j) using this univariate distribution of points to construct confidence limits;

(k) identifying as abnormal the adulterated sample, the point of which falls three central 68% quantiles outside of the cluster of points yielded by the replicate spectra obtained from the training set sample replicates of the training set.

* * * * *

UNITED STATES PATENT AND TRADEMARK OFFICE
CERTIFICATE OF CORRECTION

PATENT NO. : 4,893,253

DATED : January 9, 1990

INVENTOR(S) : Lodder

It is certified that error appears in the above-identified patent and that said Letters Patent is hereby corrected as shown below:

```
In the Abstract line 11   ---specturm--- should be ---spectrum
                             ---;
   Col. 1 line 37 ---TYLENOL, acetaminophen--- should be
                  ---TYLENOL acetaminophen,---;
   Col. 1 line 39 insert ---acetaminophen--- after ---TYLENOL---
   Col. 1 line 41 insert ---acetaminophen--- after ---TYLENOL---
   Col. 1 line 47 insert ---acetaminophen--- after ---TYLENOL---
   Col. 2 line 2 ---aceteminophen--- should be ---acetaminophen
                    ---;
   Col. 8 line 50 ---Corps.--- should be ---Corp.---;
   Col. 9 line 9 ---cemical--- should be ---chemical---;
   Col. 11 line 61 ---ANACIN--- should be ---ANACIN-3---;
   Col. 14 line 12 ---ANACIN--- should be ---ANACIN-3---; and
   Col. 14 line 23 ---ANACIN--- should be ---ANACIN-3---.
```

Signed and Sealed this

Eighteenth Day of June, 1991

Attest:

HARRY F. MANBECK, JR.

*Attesting Officer*          *Commissioner of Patents and Trademarks*